United States Patent [19]

Sokolowski

[11] E Re. 30,439

[45] Reissued Nov. 25, 1980

[54] TREATMENT OF GENITAL TRACT DISEASES OF DOMESTIC ANIMALS WITH PROSTAGLANDINS

[75] Inventor: James H. Sokolowski, Portage, Mich.

[73] Assignee: The Upjohn Company, Kalamazoo, Mich.

[21] Appl. No.: 19,524

[22] Filed: Mar. 12, 1979

Related U.S. Patent Documents

Reissue of:

[64] Patent No.: 4,051,238
Issued: Sep. 27, 1977
Appl. No.: 692,440
Filed: Jun. 3, 1976

[51] Int. Cl.[2] ..... A61K 31/20; A61K 31/43; A61K 31/71; A61K 31/215

[52] U.S. Cl. ..... 424/181; 424/227; 424/250; 424/271; 424/274; 424/248.55; 424/305; 424/316; 424/317; 424/318; 424/324

[58] Field of Search ..... 424/305, 317, 318, 271, 424/227, 18, 324, 316, 248, 274, 250

[56] References Cited

PUBLICATIONS

Bärkström et al., Vet. Bull. 44:808 (1974).

Bärkström, Proc. XII Nordie Vet. Congress, 1974, p. 277.

Hinman—Annual Review of Biochemistry, vol. 41, (1972), p. 168.

*Primary Examiner*—Stanley J. Friedman

*Attorney, Agent, or Firm*—Robert A. Armitage

[57] ABSTRACT

The treatment of purulent diseases of the female genital track of domestic animals by administration of an amount of a domestic animal luteolytic-uterine smooth muscle stimulating prostaglandin (DALUSMUS-PG) effective to cure said disease is disclosed.

9 Claims, No Drawings

TREATMENT OF GENITAL TRACT DISEASES OF DOMESTIC ANIMALS WITH PROSTAGLANDINS

Matter enclosed in heavy brackets [ ] appears in the original patent but forms no part of this reissue specification; matter printed in italics indicates the additions made by reissue.

BACKGROUND OF THE INVENTION

A wide variety of genital tract diseases of female domestic animals are known to produce significant morbidity and mortality. The cervix, vagina, uterus are prime sites for the formation and development of numerous purulent genital tract diseases, such as pyometra, mucometra, metritis, endometritis, vaginitis, and cervicitis.

The diagnosis and treatment of each of the above named diseases is readily accomplished by a veterinarian ordinarily skilled in the treatment of domestic animals. Such a [diagonis] *diagnosis* and treatment proceeds from a recognition of the known characteristics of each of these diseases and the employment of one of the known modalities of treatment. For example, ovariohysterectomy is employed in pyometra and mucometra, and chronic cases of metritis. However, this use of surgery, aside from the obvious destruction of the animal's reproductive potential, is not indicated in many cases for economic reasons, thus necessitating the sacrifice or other disposition of the animal. In other genital tract diseases, such as acute episodes of metritis, endometritis, cervicitis and vaginitis, treatment with antibiotics is often successfully, although for severe or chronic cases surgical treatment is required if the animal is to be restored to good health.

Both naturally occuring prostaglandins and prostaglandin analogs are known in the art. The naturally occuring prostaglandins have the prostanoic acid skelton, and carbon atom numbering illustrated by formula I:

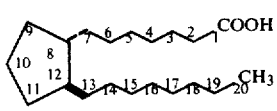

I

See Bergström, et al. Pharmacol. Rev. 20, 1 (1968) and references cited therein. For example, prostaglandin $E_2$ ($PGE_2$) exhibits the following structure:

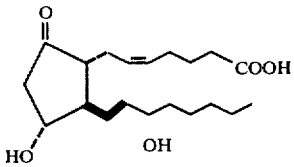

The term prostaglandin analog herein refers to those compounds structurally related to the prostaglandins (in that they exhibit a cyclopentane, or adjacently homologous cycloalkane, ring and a pair of side chains attached to adjacent carbon atoms of the ring) which retain characteristic biological properties of the prostaglandins. See Bergström, cited above. Various structural modifications of the prostaglandins are known to produce useful prostaglandin analogs. For example, the replacement of the carboxy with a hydroxymethyl or aminomethyl is known; substitution of a methyl, ethyl, or fluoro for a hydrogen at, for example, C-2 or C-16, and replacement of a methylene by an oxa or thia at, for example C-5 is known. Further, partially deoxygenated prostaglandins are known to be useful prostaglandin analogs. Accordingly, 9-deoxy, 11-deoxy, and 15-deoxy-prostaglandins are known. Further, there are known prostaglanin analogs wherein the double bonds of, for example, $PGF_{2\alpha}$ are shifted, e.g., cis-4,5-didehydro-$PGF_{1\alpha}$, or replaced by triple bonds, e.g., 13,14-didehydro-$PGF_{2\alpha}$. Finally there are known bicyclic large ringed lactones wherein the C-1 carboxyl forms a lactone with a ring or side chain hydroxyl, at C-9, C-11, or C-15.

As used herein, the term prostaglandin-type compound refers to any prostaglandin or prostaglandin-analog.

The use of prostaglandins in domestic animals, especially in regulation of the reproductive cycle, is known in the art. See, for example Lauderdale, J. W., J. Anim. Sci. 35:426 (1972); Lauderdale, J. W. et al., J. Anim. Sci. 38:964 (1974); Miller, R. A., et al., J. Anim. Sci. 41:369 (1975); and Hafez, Ed., Reproduction of Farm Animals, 3rd. Edition, Lea and Febizer, (1974), pp. 432–436 and references cited therein which describe method of administration and the effect of subcutaneous or intramuscular injection of the tris(hydroxymethyl)aminomethane (THAM) salt of $PGF_{2\alpha}$ on the estrus cycle of domestic animals and discuss the desirability and usefulness of such activity.

SUMMARY OF THE INVENTION

The present invention comprises:

a method for treating a female domestic animal suffering from a purulent genital tract disease which comprises:

administering to said animal an amount of a domestic animal luteolytic-uterine smooth muscle stimulating prostaglandin (DALUSMUS-PG) effective to cure said disease.

The present invention simply and effectively treats various purulent diseases of the female domestic animal genital tract, but does not require the use of surgical techniques which are often otherwise required. Accordingly, the present invention avoids the disadvantages in this prior art treatment: the threat to the life of the disease-compromised animal, the destruction of its reproductive potential and the uneconomic nature of the treatment due to the high cost of animal surgery. The present invention thus provides a surprising and unexpected advance in the treatment of these diseases.

Domestic animals within the scope of the present invention include sheep, cattle, horses, swine, and particularly and especially dogs and cats, the latter exhibiting an especially high incidence of the above diseases. Further, as used herein, the term "domestic animal" is further extended to include those mammals held in captivity by man, as for example, in zoological parks.

Those prostaglandin-type compounds effective for the present purpose are the domestic animal luteolytic-uterine smooth muscle stimulating prostaglandins (DALUSMUS-PG's), which are herein defined to be those prostaglandin-type compounds known in the art which are at least 30 to 50 percent as active as $PGF_{2\alpha}$ in a standard laboratory assay for determining smooth muscle and luteolytic effects of prostaglandin-type compounds on mammals. In particular, the DALUS- MUS-PG's are readily and efficiently identified by comparing the potency of any prostaglandin-type compound to $PGF_{2\alpha}$ in a gerbil colon smooth muscle assay and a hamster antifertility assay, respectively. Methods for effecting these comparisons are readily available to those of ordinary skill in the art. See Weeks, et al., J. Pharmacol. acol. Exp. Ther. 186:64–74 (1973) for a description of a gerbil colon smooth muscle assay and J. Pharm. and Exp. Ther. 186:67 (1973), for a description of a hamster antifertility assay. Accordingly, any prostaglandin-type compound exhibiting at least 30 percent to 50 percent of the potency of $PGF_{2\alpha}$ in both of these screens represents a DALUSMUS-PG. Particularly and especially preferred for the present purposes are DALUSMUS-PG's wherein the potency in either of these screens is at least 100 percent of the potency of $PGF_{2\alpha}$, for example, $PGF_{2\alpha}$, THAM salt.

Examples of prostaglandin-type compounds which are DALUSMUS-PG's are:

8β,12α-$PGE_1$, methyl ester;
17-phenyl-18,19,20-trinor-8β,12α-$PGE_1$, methyl ester;
17-phenyl-18,19,20-trinor-13,14-dihydro-8β,12α-$PGE_1$, methyl ester;
15-methyl-8β,12α-$PGE_1$, methyl ester;
15-Methyl-cis-4,5-didehydro-$PGE_1$, methyl ester;
16,16-Dimethyl-cis-4,5-didehydro-$PGE_1$, methyl ester;
17-Phenyl-18,19,20-trinor-cis-4,5-didehydro-$PGE_1$, methyl ester;
5-Oxa-16-(p-fluorophenoxy)-17,18,19,20-tetranor-$PGE_1$, methyl ester;
15-Methyl-$PGE_1$;
16-Phenoxy-17,18,19,20-tetranor-$PGE_1$;
cis-4,5-Didehydro-16,16-dimethyl-$PGE_1$;
2,2-Difluoro-15-methyl-$PGE_1$, methyl ester;
16,16-Difluoro-5-oxa-$PGE_1$, methyl ester;
16,16-Difluoro-13,14-dihydro-$PGE_1$, methyl ester;
15-Methyl-$PGE_2$;
16-Methyl-$PGE_2$;
15-Methyl-$PGE_2$, methyl ester;
16,16-Dimethyl-$PGE_2$;
17-Phenyl-18,19,20-trinor-$PGE_2$;
8β,12α-$PGE_2$, methyl ester
17-Cyclohexyl-18,19,20-trinor-$PGE_2$;
15-Methyl-8β,12α-$PGE_2$, methyl ester;
15-Methyl-$PGE_2$, isopropyl ester;
15-Methyl-$PGE_2$, p-acetamidophenyl ester;
17-Phenyl-18,19,20-trinor-8β,12α-$PGE_2$, methyl ester;
11-Deoxy-16,16-dimethyl-$PGE_2$;
16,16-Difluoro-$PGE_2$, methyl ester;
15-epi-cis-13-16,16-Difluoro-$PGE_2$, methyl ester;
16-Phenoxy -17,18,19,20-tetranor-$PGE_2$;
15-epi-16-phenoxy-17,18,19,20-tetranor-8β,12α-$PGE_2$, methyl ester;
16-Phenoxy-17,18,19,20-tetranor-8β,12α-$PGE_2$, methyl ester;
17-Phenyl-18,19,20-trinor-8β,12α-$PGE_2$;
8β,12α-$PGE_2$;
15-epi-cis-13-$PGE_2$, methyl ester;
13,14-Didehydro-$PGE_2$, methyl ester;
17-Phenyl-18,19,20-trinor-$PGE_2$, p-acetylphenyl ester;
15-methyl-17-phenyl-18,19,20-trinor-$PGE_2$, methyl ester;
17,18,19,20-Tetranor-16-phenoxy-$PGE_2$, p-acetylphenyl ester;
11-Deoxy-16-phenoxy-17,18,19,20-tetranor-$PGE_2$;
15-Methyl-16-phenoxy-17,18,19,20-tetranor-$PGE_2$, methyl ester;
15-epi-15-Methyl-16-phenoxy-17,18,19,20-tetranor-$PGE_2$, methyl ester;
2a,2b-Dihomo-17,18,19,20-tetranor-16-phenoxy-$PGE_2$;
11-Deoxy-16,16-difluoro-$PGE_2$, methyl ester;
2a,2b-Dihomo-15-methyl-17-phenyl-18,19,20-trinor-$PGE_2$, methyl ester;
13,14-Didehydro-$PGE_2$;
16-(m-chlorophenoxy)-17,18,19,20-tetranor-$PGE_2$;
2,2-Difluoro-16-(m-trifluoromethyl phenoxy)-17,18,19,20-tetranor-$PGE_2$, 15-methyl ether, methyl ester;
2,2,16,16-Tetrafluoro-$PGE_2$, methyl ester;
15-epi-cis-13[,]-2,2-Difluoro-$PGE_2$, methyl ester;
16,16-Difluoro-13,14-dihydro-$PGE_2$, methyl ester;
racemic-17-Phenyl-18,19,20-trinor-$PGF_{1\alpha}$;
15-Methyl-$PGF_{1\alpha}$;
racemic-15-methyl-17-phenyl-18,19,20-trinor-$PGF_{1\alpha}$;
15-Methyl-$PGF_{1\alpha}$, methyl ester;
cis-4,5-Didehydro-$PGF_{1\alpha}$;
5-oxa-$PGF_{1\alpha}$;
17-Phenyl-18,19,20-trinor-$PGF_{1\alpha}$;
13,14-Dihydro-17-phenyl-18,19,20-trinor-$PGF_{1\alpha}$;
15-Methyl-cis-4,5-didehydro-$PGF_{1\alpha}$, methyl ester;
cis-4,5-Didehydro-$PGF_{1\alpha}$, methyl ester;
16,16-Dimethyl-cis-4,5-didehydro-$PGF_{1\alpha}$, methyl ester;
5-oxa-16-(p-fluorophenoxy)-17,18,19,20-tetranor-$PGF_{1\alpha}$, methyl ester;
cis-4,5-Didehydro-16,16-dimethyl-$PGF_{1\alpha}$;
15-Methyl-cis-4,5-didehydro-$PGF_{1\alpha}$;
$PGF_{2\alpha}$;
$PGF_{2\alpha}$, 1-lysine salt;
$PGF_{2\alpha}$, 1-arginine salt;
5,6-trans-$PGF_{2\alpha}$;
15-Methyl-$PGF_{2\alpha}$;
17-Phenyl-18,19,20-trinor-$PGF_{2\alpha}$, methyl ester;
17-Phenyl-18,19,20-trinor-$PGF_{2\alpha}$;
20-Ethyl-$PGF_{2\alpha}$;
15-Methyl-$PGF_{2\alpha}$, methyl ester;
17-Phenyl-18,19,20-trinor-$PGF_{2\alpha}$, 15-methyl ether;
20-Methyl-$PGF_{2\alpha}$;
16,16-Dimethyl-$PGF_{2\alpha}$;
16-Methyl-$PGF_{2\alpha}$;
16-Methyl-16-phenoxy-18,19,20-trinor-$PGF_{2\alpha}$;
15-Methyl-15-epi-$PGF_{2\alpha}$, methyl ester;
16,16-Dimethyl-17-phenyl-18,19,20-trinor-$PGF_{2\alpha}$;
$PGF_{2\alpha}$, 15-methyl ether;
16-Phenoxy-17,18,19,20-tetranor-$PGF_{2\alpha}$;
$PGF_{2\alpha}$, isopropyl ester;
15-methyl-17-phenyl-18,19,20-trinor-$PGF_{2\alpha}$, methyl ester;
16-Fluoro-$PGF_{2\alpha}$;
13,14-Dihydro-$PGF_{2\alpha}$;
17-p-chlorophenyl-18,19,20-trinor-$PGF_{2\alpha}$, ethyl ester;
16,16-Dimethyl-$PGF_{2\alpha}$, methyl ester;
16-Methyl-16-phenoxy-18,19,20-trinor-$PGF_{2\alpha}$, methyl ester;
17-Cyclohexyl-18,19,20-trinor-$PGF_{2\alpha}$;
20-Ethyl-15-methyl-$PGF_{2\alpha}$, methyl ester,
17-(p-fluorophenyl)-18,19,20-trinor-$PGF_{2\alpha}$;
15-epi-2,2-difluoro-15-methyl-$PGF_{2\alpha}$, methyl ester;
2,2-Difluoro-15-methyl-$PGF_{2\alpha}$, methyl ester;
15-Methyl-11β-$PGF_{2\alpha}$, methyl ester;
2,2-Difluoro-17-phenyl-18,19,20-trinor-$PGF_{2\alpha}$, methyl ester;
15-Methyl-13,14-dihydro-$PGF_{2\alpha}$, methyl ester;
15 -Methyl-$PGF_{2\alpha}$, methyl ester, 15-methyl ether;

13,14-Didehydro-15-epi-$PGF_{2\alpha}$, methyl ester;
15-epi-cis-13-16,16-Difluoro-$PGF_{2\alpha}$, methyl ester;
15-epi-16,16-Difluoro-$PGF_{2\alpha}$, methyl ester;
2-Decarboxy-2-hydroxymethyl-16,16-dimethyl-$PGF_{2\alpha}$;
$PGF_{2\alpha}$, p-acetamidophenyl ester;
$PGF_{2\alpha}$, biphenyl ester;
$PGF_{2\alpha}$, p-benzaldehyde semicarbazone ester;
15-epi-15-Ethyl-$PGF_{2\alpha}$, methyl ester;
16,16,15-Trimethyl-$PGF_{2\alpha}$, methyl ester;
13,14-Didehydro-$PGF_{2\alpha}$, methyl ester;
(12E)-12,13-Didehydro-13,14-dihydro-15-methyl-$PGF_{2\alpha}$, methyl ester;
15-epi-cis-13-$PGF_{2\alpha}$, methyl ester;
13,14-Dihydro-17-phenyl-18,19,20-trinor-$PGF_{2\alpha}$;
15-epi-cis-13-16-(p-fluorophenoxy)-17,18,19,20-tetranor-$PGF_{2\alpha}$, methyl ester;
15-epi-cis-13-$PGF_{2\alpha}$;
16-(m-trifluoromethylphenoxy)-17,18,19,20-tetranor-$PGF_{2\alpha}$;
15-Methyl-$PGF_{2\alpha}$, naphthyl ester;
15-Methyl-$PGF_{2\alpha}$, p-acetyl phenyl ester;
2-Decarboxy-2-aminomethyl-$PGF_{2\alpha}$;
11$\beta$-16,16-Dimethyl-$PGF_{2\alpha}$, methyl ester;
15-Methyl-16-phenoxy-17,18,19,20-tetranor-$PGF_{2\alpha}$,-methyl ester;
15-epi-15-Methyl-16-phenoxy-17,18,19,20-tetranor-$PGF_{2\alpha}$, methyl ester;
13,14-Dihydro-2,2-difluoro-$PGF_{2\alpha}$, methyl ester;
2a,2b-Dihomo-17,18,19,20-tetranor-16-phenoxy-$PGF_{2\alpha}$;
2-Decarboxy-2-aminomethyl-16,16-dimethyl-$PGF_{2\alpha}$;
2-Decarboxy-2-aminomethyl-15-methyl-$PGF_{2\alpha}$;
2a,2b-Dihomo-15-methyl-17-phenyl-18,19,20-trinor-$PGF_{2\alpha}$, methyl ester;
13,14-Didehydro-$PGF_{2\alpha}$;
11-Deoxy-16,16-difluoro-$PGF_{2\alpha}$, methyl ester;
2,2,16,16-Tetrafluoro-$PGF_{2\alpha}$, methyl ester;
16-(m-chlorophenoxy)-17,18,19,20-tetranor-$PGF_{2\alpha}$;
15-epi-cis-13-2,2-Difluoro-$PGF_{2\alpha}$, methyl ester;
2,2-Difluoro-16-(m-trifluoromethylphenoxy)-17,18,19,20-tetranor-$PGF_{2\alpha}$, 15-methyl ether, methyl ester;
$PGF_{2\alpha}$, 2-methyl phenyl ester;
$PGF_{2\alpha}$, 2,6-dimethyl phenyl ester;
$PGF_{2\alpha}$, Phenyl ester;
16,16-Difluoro-13,14-dihydro-$PGF_{2\alpha}$, methyl ester;
13,14-Dihydro-15-epi-15-methyl-$PGF_{2\alpha}$;
17-Phenyl-18,19,20-trinor-8$\beta$,12$\alpha$-$PGF_{2\alpha}$, methyl ester; and
16-Phenoxy-17,18,19,20-tetranor-8$\beta$,12$\alpha$-$PGF_{2\alpha}$, methyl ester.

The above DALUSMUS-PG's are all named essentially according to the system of nomenclature described by Nelson, J. Med. Chem. 17:911 (1974).

With regard to the above list of DALUSMUS-PG's, various known pharmacologically acceptable salts are used in place of the free acids or methyl esters enumerated above. Examples of such known salts are those with pharmaceutically acceptable metal cations, ammonium amine cations, quaternary ammonium cations, and basic amino acid cations.

Known among the pharmaceutically acceptable metal cations of prostaglandin salts are those derived from the alkali metals, e.g., lithium, sodium, and potassium, and from the alkaline earth metals, e.g., magnesium and calcium, and also the cationic forms of other metals, e.g., aluminum, zinc, and iron.

Known among the pharmaceutically acceptable amine cations are those derived from primary, secondary, or tertiary amines. Examples of suitable amines are methylamine, dimethylamine, trimethylamine, ethylamine, dibutylamine, triisopropylamine, N-methyl hexylamine, decylamine, dodecylamine, allylamine, crotylamine, cyclopentylamine, dicyclohexylamine, benzylamine, dibenzylamine, $\alpha$-phenylethylamine, $\beta$-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, amantadine and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglucamine, N-methylglucosamine, ephedrine, phenylephrine, epinephrine, procaine, and the like.

Known among the pharmaceutically acceptable quaternary ammonium cations are tetramethylammonium, tetraethylammonium, benzyltrimethylammonium, phenyltriethylammonium, and the like.

Known among the basic amino acid cations are arginine and lysine.

The purulent genital tract diseases of female domestic animals are those described above, particularly in the Background of The Invention.

Finally, the present invention requires the use of an amount of DALUSMUS-PG which is effective to cure the purulent genital tract disease. For this purpose a wide variety of dosage schedules and routes of administration are employed. For convenience, however, the DALUSMUS-PG is preferably administered either one or twice daily. The treatment regiment is continued until the clinical manifestations of the disease begin to subside, ordinarily after 1 to 2 days of treatment. However, the treatment is repeated within 5 to 10 days after the initial administration if during this period the regression of the clinical symptoms of the disease is incomplete.

In situations where the animal is under veterinary care the preferred route of administration is parenteral, especially intermuscular and subcutaneous. In this case, the DALUSMUS-PG is conventially formulated for parenteral administration by known methods.

However, other routes of administration can be employed when the parenteral route is not convenient. Thus oral formulation (in liquids or tablets) or vaginal formulation (preferably as suppositories, although DALUSMUS-PG-impregnated silastic devices are also employed) are undertaken and administration is effected by these routes.

Effective dosage of the DALUSMUS-PG depends upon the potency of the DALUSMUS-PG relative to $PGF_{2\alpha}$, for which doses on the order to 1.0 mg./kg./day for subcutaneous or intramuscular administration are employed. However, for any animal the dosages are varied within a wide range when in the opinion of the attending veterinarian the animal is receiving too little PG (i.e., therapeutic progress is too slow or absent) or too much PG (i.e., side effects, notably diarrhea and vomiting, are too intense or too prolonged after administration). Thus for $PGF_{2\alpha}$ doses in the range of 0.01–1.0 mg./kg./day are employed. Further employing oral or vaginal routes of administration require somewhat higher doses of DALUSMUS-PG than are required by parenteral administration, i.e. from two to 10 times the corresponding dose.

For DALUSMUS-PG's other than $PGF_{2\alpha}$, the dosage is readily determined by the attending veterinarian, employing known methods. Thus, for example, the veterinarian would initiate treatment at the low end of the dosage range for $PGF_{2\alpha}$, and thereafter rapidly adjust the dosage upward or downward, based on animal response, as described above. In any event for DALUSMUS-PG's other than $PGF_{2\alpha}$ the parenteral dose should not exceed 10 times the maximum dose of $PGF_{2\alpha}$ indicated above.

A further aspect of the present invention is the concomitant administration of antibiotic with the DALUSMUS-PG, in an amount effective to treat or prevent an infection associated with the purulent genital tract disease. Preferred antibiotics are a penicillin, a tetracycline, lincomycin, clindamycin, chloramphenicol, and streptomycin.

The use of the antibiotic is either therapeutic (i.e., in the amount known to be useful in treatment of an existing infectious condition) or prophylactic (i.e., in an amount effective to prevent or forestall the development of an infection associated with the purulent genital tract disease). When employed therapeutically, the preferred method of treatment requires a culture to be taken which will determine antibiotic sensitivity to the infecting organism and thus aid in a rational selection of the antibiotic.

As employed concomitantly, the antibiotic can be administered by the same or a different route as the DALUSMUS-PG, but in any case as is known in the art for antibiotics administration to animals.

I claim:

[1. A method for treating a female domestic animal suffering from a purulent genital tract disease which comprises:

administering to said animal an amount of a domestic animal luteolytic-uterine smooth muscle stimulating prostaglandin (DALUSMUS-PG) effective to cure said disease.]

[2. A method according to claim 1 which further comprises concomitantly administering an amount of an antibiotic effective to treat or prevent an infection associated with said purulent genital tract disease.]

[3. A method according to claim 2 wherein said purulent genital tract disease is endometritis.]

[4. A method according to claim 2 wherein said purulent genital tract disease is metritis.]

[5. A method according to claim 2 wherein said purulent genital tract disease is mucometra.]

[6. A method according to claim 2 wherein said genital tract disease is pyometra.]

[7. A method according to claim 6 wherein said female domestic animal is bovine, equine, or swine.]

[8. A method according to claim 6 wherein said domestic animal is canine or feline.]

[9. A method according to claim 8 wherein said DALUSMUS-PG is 15-methyl-$PGF_{2\alpha}$, THAM salt.]

[10. A method according to claim 8, wherein said DALUSMUS-PG is $PGF_{2\alpha}$, THAM salt or $PGF_{2\alpha}$, l-arginine salt.]

[11. A method according to claim 1 wherein said DALUSMUS-PG is at least as potent as $PGF_{2\alpha}$ in a gerbil colon smooth muscle assay or a hamster anifertility assay.]

[12. A method according to claim 1 wherein said DALUSMUS-PG is at least as potent as $PGF_{2\alpha}$ in both a gerbil colon smooth muscle assay and a hamster antifertility assay.]

[13. A method according to claim 12 wherein said purulent genital tract disease is endometritis.]

[14. A method according to claim 12 wherein said purulent genital tract disease is metritis.]

[15. A method according to claim 12 wherein said purulent genital tract disease is mucometra.]

[16. A method according to claim 12 wherein said genital tract disease is pyometra.]

[17. A method according to claim 16 wherein said female domestic animal is bovine, equine, or swine.]

[18. A method according to claim 16 wherein said domestic animal is canine or feline.]

[19. A method according to claim 18 wherein said DALUSMUS-PG is 15-methyl-$PGF_{2\alpha}$, THAM salt.]

[20. A method according to claim 18 wherein said DALUSMUS-PG is $PGF_{2\alpha}$, THAM salt or $PGF_{2\alpha}$, l-arginine salt.]

*21. A method for treating a female domestic dog or cat suffering from a purulent genital tract disease which comprises:*

*administering to said dog or cat an amount of a domestic animal luteolytic-uterine smooth muscle stimulating prostaglandin (DALUSMUS-PG) effective to cure said disease.*

*22. A method according to claim 21, wherein said DALUSMUS-PG is at least as potent as $PGF_{2\alpha}$ in a gerbil colon smooth muscle assay or a hamster antifertility assay.*

*23. A method according to claim 21, wherein said DALUSMUS-PG is at least as potent as $PGF_{2\alpha}$ in both a gerbil colon smooth muscle assay and a hamster antifertility assay.*

*24. A method according to claim 23, wherein said purulent genital tract disease is endometritis.*

*25. A method according to claim 23, wherein said purulent genital tract disease is metritis.*

*26. A method according to claim 23, wherein said purulent genital tract disease is mucometra.*

*27. A method according to claim 23, wherein said genital tract disease is pyometra.*

*28. A method according to claim 27, wherein said DALUSMUS-PG is 15-methyl-$PGF_{2\alpha}$, THAM salt.*

*29. A method according to claim 27, wherein said DALUSMUS-PG is $PGF_{2\alpha}$, THAM salt or $PGF_{2\alpha}$, l-arginine salt.*

* * * * *